(12) United States Patent
Hochrein et al.

(10) Patent No.: US 11,097,040 B2
(45) Date of Patent: Aug. 24, 2021

(54) APPARATUS FOR DETERMINING THE PERITONEAL PRESSURE

(71) Applicant: FRESENIUS MEDICAL CARE DEUTSCHLAND GMBH, Bad Homburg (DE)

(72) Inventors: Torsten Hochrein, Eschenau (DE); Frank Hedmann, Volkach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 611 days.

(21) Appl. No.: 15/503,503

(22) PCT Filed: Aug. 10, 2015

(86) PCT No.: PCT/EP2015/001647
§ 371 (c)(1),
(2) Date: Feb. 13, 2017

(87) PCT Pub. No.: WO2016/023632
PCT Pub. Date: Feb. 18, 2016

(65) Prior Publication Data
US 2017/0232176 A1    Aug. 17, 2017

(30) Foreign Application Priority Data
Aug. 13, 2014   (DE) ............... 10 2014 012 024.4

(51) Int. Cl.
*A61M 1/28*     (2006.01)
*G16H 20/40*    (2018.01)

(52) U.S. Cl.
CPC ............. *A61M 1/282* (2014.02); *A61M 1/28* (2013.01); *G16H 20/40* (2018.01);
(Continued)

(58) Field of Classification Search
CPC ........ A61M 1/28; A61M 1/282; A61M 1/284; A61M 1/285; A61M 1/287; A61M 1/288
See application file for complete search history.

(56) References Cited

U.S. PATENT DOCUMENTS 5,141,493 A * 8/1992 Jacobsen ............. A61M 1/1696
                                                   210/104
6,228,047 B1   5/2001 Dadson
(Continued)

FOREIGN PATENT DOCUMENTS

DE    102008031662    1/2010
JP    2000084070      3/2000

*Primary Examiner* — Nathan R Price
*Assistant Examiner* — Courtney B Fredrickson
(74) *Attorney, Agent, or Firm* — Jacobson Holman PLLC

(57) ABSTRACT

An apparatus for determining at least one of the peritoneal pressure in the abdomen of a patient, and the drainage state of the abdomen of a patient, includes at least one pump for conveying a dialysis solution into the abdomen, and at least one measurement device for measuring the pressure in the dialysis solution. The apparatus has at least one control unit configured to control the pump and the measurement device such that a first measurement of the pressure is carried out by the measurement device with a stationary pump to obtain a first measured pressure value. The pump subsequently operates to convey a partial volume of the total inflow volume of the dialysis solution into the abdomen. The pump then stops, and a second measurement of the pressure is carried out by the measurement device to obtain a second measured pressure value.

13 Claims, 2 Drawing Sheets

(52) U.S. Cl.
CPC . *A61M 2205/18* (2013.01); *A61M 2205/3344* (2013.01); *A61M 2205/3379* (2013.01); *A61M 2205/50* (2013.01)

(56) References Cited

U.S. PATENT DOCUMENTS

| | | | |
|---|---|---|---|
| 9,061,099 B2 * | 6/2015 | Gerber | A61B 5/0031 |
| 2003/0220606 A1 * | 11/2003 | Busby | A61M 1/28 604/29 |
| 2010/0004590 A1 * | 1/2010 | Hedmann | A61M 1/28 604/29 |

* cited by examiner

APPARATUS FOR DETERMINING THE PERITONEAL PRESSURE

BACKGROUND OF THE INVENTION

1. Field of the Invention

The present invention relates to an apparatus for determining the peritoneal pressure in the abdomen of a patient and/or for determining the drainage state of the abdomen of a patient, wherein the apparatus comprises at least one pump for conveying a dialysis solution into the abdomen as well as at least one measurement device for measuring the pressure in the dialysis solution.

2. Description of Related Art

Within the framework of a peritoneal dialysis treatment, a volume of dialysis fluid is introduced into the abdomen of a patient and is left there for a specific dwell time. The peritoneum acts as a semipermeable membrane that allows a mass transfer from the blood into the dialysis fluid, whereby a blood purification is achieved.

A vacuum arises during the complete outflow, i.e. during the discharge of the dialysis solution from the abdomen. This pressure measured in the dialysis solution is composed of the dynamic pressure caused by the flow of the dialysis solution, of the static pressure caused by the position of the patient, and of the pressure in the abdomen, i.e. of the peritoneal pressure.

Since the measured pressure thus comprises a plurality of components, the dialysis machine cannot make a clear association, i.e. cannot make any statement on how high the peritoneal pressure is that is a measure for the drainage of the abdomen of the patient. Nor can a statement easily be made from the total measured pressure on the extent to which the abdomen has been drained.

SUMMARY OF THE INVENTION

It is thus the underlying object of the present invention to further develop an apparatus of the originally named kind such that a determination of the peritoneal pressure and/or of the drainage state of the patient is possible.

This object is achieved by an apparatus having the features described herein. Provision is accordingly made that the apparatus comprises at least one control unit that is configured such that is controls the pump and the measurement device such that a first measurement of the pressure of the dialysis solution is carried out by the measurement device with a stationary pump to obtain a first measured pressure value and such that it subsequently sets the pump into operation to convey a part volume of the total inflow volume of the dialysis solution into the abdomen and then stops the pump. The control unit is furthermore designed such that a second measurement of the pressure of the dialysis solution is carried out by the measurement device to obtain a second measured pressure value.

The control unit is thus configured such that it carries out a specific method, with this method comprising a first pressure measurement in the dialysis solution when the dialysis solution is not flowing, with the method furthermore comprising the inflow of a part volume of the total inflow volume intended for the patient by means of a pump, the stopping of the pump and a second pressure measurement in the dialysis solution.

If the differential pressure between the two pressure measurements is small, there is no vacuum or no significant vacuum in the abdomen, i.e. the measured pressure is due to the position of the patient.

If the differential pressure between the two pressure measurements is large, there is a vacuum in the abdomen and the first measured pressure value reflects the peritoneal pressure.

The conveying pressure of a pump, i.e. the dynamic pressure, does not play any role in the two pressure measurements since the dialysis solution is stationary due to the stationary pump.

It is possible by the described procedure to carry out a determination of the peritoneal pressure that can then, for example, be stored in the apparatus or can be processed in an evaluation device.

The described procedure furthermore allows conclusions on the drainage state of the abdomen. If the differential pressure between the two pressure measurements is large, this is an indication that the abdomen was completely drained in the preceding drainage. If the differential pressure between the two pressure measurements is, however, small, this indicates that a specific volume of the dialysis solution was or still is present in the abdomen.

It is possible by the apparatus in accordance with the invention to associate the pressure measured in the course of a treatment. As stated, it can be determined with reference to the two pressure measurements whether the measured pressure is the peritoneal pressure and/or what drainage state the abdomen has.

The volume conveyed into the abdomen by the apparatus can remain in the abdomen. After the completed second pressure measurement, the remaining portion of the total inflow volume can be conveyed into the abdomen, for which purpose the pump is correspondingly controlled by the said control unit.

The conveyed partial volume can be selected as larger so that a "local pressure" in a "peritoneum pocket" can be precluded.

There is a further advantage that pressure alarms that occur no longer have to be acknowledged by a user, which reduces the number of interactions between the apparatus and the user. This is in particular desirable on a carrying out of a peritoneal dialysis carried out by the apparatus at night.

The independent resetting of errors is thereby made possible in that the apparatus has the capability of being able to estimate the measured pressure value due to the second pressure measurement or due to the comparison of the two pressure measurements. The number of pressure alarms can therefore be reduced or pressure alarms that occur can be subjected to a plausibility check by the apparatus itself and can optionally be acknowledged by the apparatus itself.

If such a plausibility check were not possible and if the apparatus were to reset an alarm without such a check, this bears the risk that dangerous situations are not signaled to the user or that these situations are not resolved or are even amplified.

In general, exactly two measured pressure values or also more than two measured pressure values can be determined. In the second case, more than two measured pressure values can thus also be compared with one another to be able to draw conclusions on the drainage state of the abdomen and/or on the peritoneal pressure.

The control unit of the apparatus can be configured such that the partial volume conveyed by the pump does not exceed a specific percentage of the total inflow volume to be administered to the patient or exactly corresponds to such a percentage. It is, for example, conceivable that the partial volume that is introduced into the abdomen between the two pressure measurements amounts to 5% of the total inflow volume intended for the patient.

It is also conceivable that the control unit is configured such that the partial volume conveyed by the pump corresponds to or does not exceed a specific absolute value. It can, for example, be preset that the said partial volume amounts e.g. to 100 ml.

Provision is made in a further embodiment of the invention that the apparatus comprises at least one evaluation unit that is configured such that it determines the difference between both measured pressure values and determines the drainage state of the abdomen from the determined difference. As stated above, the evaluation unit can be configured such that it concludes a drained abdomen when the pressure difference is large. This can, for example, be signaled to the apparatus optically and/or acoustically or in another manner.

It is conceivable in this respect that the evaluation unit is configured such that a conclusion is drawn on a drained abdomen when the difference between the two pressure values exceeds a specific absolute or relative limit value. If the amount of the difference amounts, for example, to 50 mbar or more, a conclusion is drawn that the abdomen was drained on the first pressure measurement.

Provision can also be made, instead of using an absolute pressure value as the basis, that the pressure difference is put into relation with the measured first or second pressure values and the relation is then used to determine the drainage state.

The aforesaid evaluation unit or also a further evaluation unit can be configured such that it determines the difference between the two pressure values and determines the peritoneal pressure from the determined difference. If the difference is large, it can be found that the first measured pressure value represents the peritoneal pressure. Whether the difference is large can be determined, for example, in that a check is made whether the difference between the two pressure values exceeds a specific absolute or relative limit value.

The apparatus can furthermore have at least one store, i.e., storage or memory in which the value of the peritoneal pressure is stored. This stored value can be used as the basis for the following drainage and filling cycles such that the apparatus can always check measured pressure values as to whether it is the peritoneal pressure in the abdomen, which has the consequence that the pump is stopped by the control unit on reaching this pressure value since the abdomen has been drained.

The present invention furthermore relates to a peritoneal dialysis machine, i.e. a dialysis machine having means for carrying out a peritoneal dialysis treatment comprising at least one apparatus as described herein. The pump and/or the measurement device can be the pump and the measurement device of the peritoneal dialysis machine, i.e. the apparatus can form an integral component of the peritoneal dialysis machine. It is, however, generally also conceivable that the pump and/or the measurement device of the apparatus is/are different elements than the pump and/or measurement device of the peritoneal dialysis machine.

The peritoneal dialysis machine can have means for generating an alarm in dependence on the measured pressure, with the means being configured such that the determined peritoneal pressure is taken into account on the generation of the alarm.

The present invention furthermore relates to a method of determining the peritoneal pressure in the abdomen of a patient and/or for determining the drainage state of the abdomen of a patient, with the method comprising the introduction of dialysis solution into the abdomen of the patient, and with the method comprising the following steps:
  a. measuring a first pressure value of the dialysis solution while the pump for conveying the dialysis solution is stationary;
  b. conveying a partial volume of the total inflow volume of the dialysis solution into the abdomen; and
  c. stopping the pump and measuring a second pressure value with a stationary pump.

The apparatus or the peritoneal dialysis machine in accordance with the invention preferably has means that are suitable and intended to carry out the method in accordance with the invention.

As stated above, provision can be made that the partial volume conveyed by the pump does not exceed a specific percentage of the total inflow volume to be administered to the patient or exactly corresponds to such a percentage. The partial volume conveyed by the pump can correspond to a specific absolute value or provision can be made that the latter is not exceeded.

The method can furthermore be configured such that the difference between both measured pressure values is determined and a conclusion is drawn on the drainage state of the abdomen from the determined difference. In this respect, a conclusion can be drawn on a drained abdomen when the difference between the two pressure values exceeds a specific absolute or relative limit value.

It is also conceivable that the difference between both pressure values is determined and the peritoneal pressure is determined from the determined difference. This corresponds to the first measured value, provided that the difference between the two pressure values is large, i.e. exceeds a specific absolute or relative limit value.

Provision is preferably made that the peritoneal pressure is considered equivalent to the first measured pressure value when the difference between the two pressure values exceeds a specific absolute or relative limit value.

The peritoneal pressure determined in this manner can be saved. It can be used in the further course of the treatment to classify the measured pressure values and to determine whether the abdomen is drained or whether this is not the case.

BRIEF DESCRIPTION OF THE DRAWINGS

Further details and advantages of the invention will be explained in more detail with reference to an embodiment shown in the drawing.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
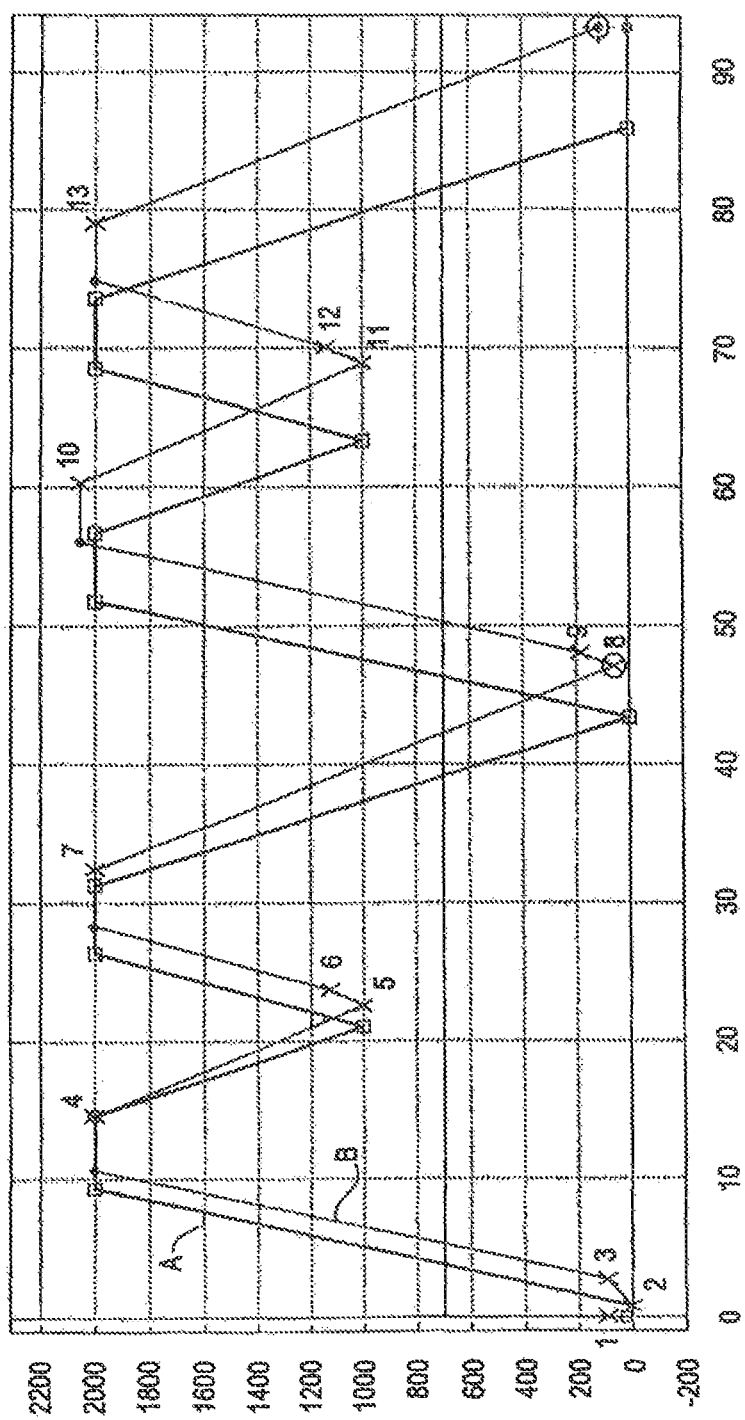
FIG. 1: the temporal desired and actual development of the filling volume in the abdomen during a peritoneal dialysis treatment.

FIG. 1 shows the treatment volume, i.e. the volume of the dialysis solution administered to the patient in the course of a peritoneal dialysis treatment over time.

In this respect, the line A represents the time development of the prescribed treatment volume and the line B represents the time development of the actually conveyed volume, i.e. the volume of dialysis solution in the abdomen of the patient.

FIG. 1 shows a so-called tidal treatment that is divided into two base cycles and two tidal cycles. In a base cycle, the abdomen of the patient is completely drained of the dialysis solution; in the tidal cycles, a residual volume of the dialysis solution remains in the abdomen, i.e. no complete drainage of the abdomen of dialysis solution takes place.

The dots X1 to X13 on the line B mark the times of the pressure measurements. The pressure values obtained in this process can be seen from FIG. 2.

At the measurement point X2, the abdomen is completely drained, i.e. there is no longer any dialysis solution in the abdomen. The pressure adopts a minimal value, as can be seen from FIG. 2. In the example shown here the vacuum amounts to approximately 92 mbar. During draining, the pressure in the abdomen or in the dialysis solution decreases greatly as can be seen from a comparison of the measurement values X1 and X2.

If, starting from the drained state of the abdomen, i.e. starting from point X2, a partial volume of dialysis solution is introduced into the abdomen, the point X3 results. In the example shown here, the partial volume amounts to approximately 100 ml.

Figure 2:
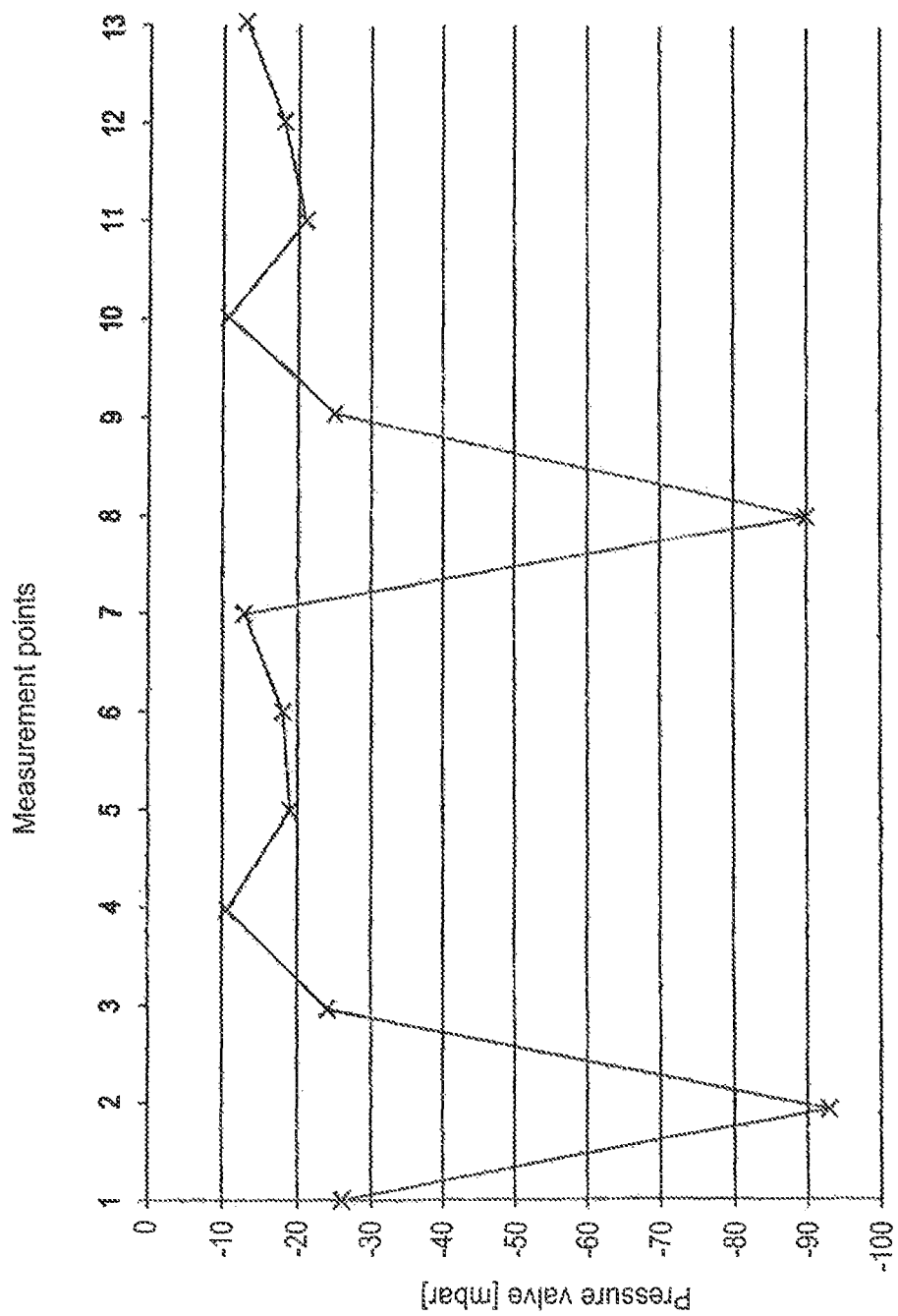
FIG. 2: the pressure values associated with the measured points in FIG. 1.

The pressure increase between the points X2 and X3 is substantial, as can be seen from FIG. 2. The same situation results for the completely drained state at measurement point X8. The supply of a quantity of dialysis solution (approx. 100 ml) that is small in comparison with the total inflow volume (approx. 2 l) produces a substantial increase in the measured pressure. This large pressure difference allows the conclusion that a complete drainage of the abdomen took place. It can be recognized in this manner that the abdomen has been drained. Apart from this, the peritoneal pressure can be determined, i.e. the pressure in the drained state of the abdomen (in the embodiment approx. 93 mbar vacuum at the measurement points X2 and X8).

The pressure measurement at X2 and X2 takes place with a stationary pump. A partial volume of the dialysis solution is subsequently introduced, the pump is stopped and the pressure is measured again (pressure measurement at X3 and at X9). As stated, it can be concluded from the pressure difference shown in FIG. 2 that the abdomen was drained.

A different situation results if, in contrast, there is still a residual volume in the abdomen, as is the case at measurement points X5 and X11, and if the method is then likewise carried out, i.e. pressure measurement in the stationary dialysis solution at X5 and X11, introduction of a partial volume by means of the pump, stopping the pump, and repeat pressure measurement at the measurement points X6 and X12.

As can be seen from FIG. 2, the pressure increase between X5 and X6 and between X11 and X12 is comparatively small. This allows the conclusion that there was no complete drainage of the abdomen at the points X5 and X11, which is correct, as can be seen from FIG. 1, since only a portion of the total dialysis solution in the abdomen was drained between the points X4 and X5 and between the points X10 and X11. The vacuum measured at X5 and X11 (approx. 20 mbar in the embodiment) is thus not representative for the peritoneal pressure.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for determining a peritoneal pressure in the abdomen of a patient, said apparatus comprising:
   a pump for conveying a dialysis solution into the abdomen;
   a measurement device for measuring a pressure of the dialysis solution;
   a control unit configured to control the pump and the measurement device such that, with the pump stationary, the measurement device carries out a first measurement of the pressure to obtain a first measured pressure value, the pump is subsequently operated to convey a partial volume of a total inflow volume of the dialysis solution into the abdomen, and then, with the pump stopped to again be stationary, the measurement device carries out a second measurement of the pressure to obtain a second measured pressure value; and
   an evaluation unit configured to determine a difference between the first measured pressure value and the second measured pressure value, and to
   determine the peritoneal pressure from the determined difference, with the first measured pressure value representing the peritoneal pressure if the determined difference exceeds a specific absolute or relative limit value.

2. The apparatus in accordance with claim 1, wherein the control unit is configured such that the partial volume conveyed by the pump does not exceed a specific percentage of an overall total inflow volume administered to the patient, or exactly corresponds to the specific percentage.

3. The apparatus in accordance with claim 1, wherein the control unit is configured such that the partial volume conveyed by the pump corresponds to or does not exceed the specific absolute value.

4. The apparatus in accordance with claim 1, wherein the evaluation unit is configured such that the peritoneal pressure is considered equivalent to the first measured pressure value when the determined difference exceeds the specific absolute or relative limit value.

5. The apparatus in accordance with claim 1, wherein the apparatus has a storage device in which the peritoneal pressure is stored.

6. A peritoneal dialysis machine comprising an apparatus in accordance with claim 1.

7. The peritoneal dialysis machine in accordance with claim 6, further comprising a device to generate an alarm based on the determined pressure.

8. The apparatus according to claim 7, wherein the device to generate the alarm is configured such that the determined peritoneal pressure is a basis for the generation of the alarm.

9. A method of determining a peritoneal pressure in the abdomen of a patient, said method comprising the steps of:
   introducing a dialysis solution into the abdomen of the patient;
   while keeping stopped a pump for conveying the dialysis solution, measuring a first pressure value of the dialysis solution;

conveying with the pump a partial volume of a total inflow volume of the dialysis solution into the abdomen;

stopping the pump, and measuring a second pressure value of the dialysis solution;

determining, with an evaluation unit, a difference between the first measured pressure value and the second measured pressure value; and determining, with the evaluation unit, the peritoneal pressure from the determined difference, with the first measured pressure value representing the peritoneal pressure if the determined difference exceeds a specific absolute or relative limit value.

10. The method in accordance with claim 9, wherein the partial volume conveyed by the pump does not exceed a specific percentage of an overall total inflow volume administered to the patient or exactly corresponds to the specific percentage.

11. The method in accordance with claim 9, wherein the partial volume conveyed by the pump corresponds to or does not exceed the specific absolute value.

12. The method in accordance with claim 9, wherein the peritoneal pressure is considered equivalent to the first measured pressure value when the difference exceeds the specific absolute or relative limit value.

13. The method accordance with claim 9, wherein the peritoneal pressure is saved as a stored value.

* * * * *